United States Patent
Lendl et al.

(10) Patent No.: US 8,872,117 B2
(45) Date of Patent: Oct. 28, 2014

(54) DEVICE FOR FTIR ABSORPTION SPECTROSCOPY

(75) Inventors: Bernhard Lendl, Vienna (AT); Stefan Radel, Vienna (AT); Markus Brandstetter, Ardagger (AT)

(73) Assignee: Technische Universitaet Wien, Vienna (AT)

( * ) Notice: Subject to any disclaimer, the term of this patent is extended or adjusted under 35 U.S.C. 154(b) by 446 days.

(21) Appl. No.: 13/143,578

(22) PCT Filed: Jan. 8, 2010

(86) PCT No.: PCT/AT2010/000006
§ 371 (c)(1),
(2), (4) Date: Jul. 7, 2011

(87) PCT Pub. No.: WO2010/078612
PCT Pub. Date: Jul. 15, 2010

(65) Prior Publication Data
US 2011/0278457 A1    Nov. 17, 2011

(30) Foreign Application Priority Data

Jan. 8, 2009 (AT) .................................... A 26/2009
Jan. 9, 2009 (AT) .................................... A 30/2009

(51) Int. Cl.
| | |
|---|---|
| *G01T 1/24* | (2006.01) |
| *H01L 27/146* | (2006.01) |
| *G01N 21/85* | (2006.01) |
| *G01N 21/15* | (2006.01) |
| *G01N 21/55* | (2014.01) |
| *G01N 21/35* | (2014.01) |

(52) U.S. Cl.
CPC ...... *G01N 21/552* (2013.01); *G01N 2021/3595* (2013.01); *G01N 21/8507* (2013.01); *G01N 21/15* (2013.01); *G01N 2201/021* (2013.01); *G01N 2021/154* (2013.01)
USPC ............. 250/370.08; 250/370.11; 250/370.09

(58) Field of Classification Search
USPC ........................... 250/339.11, 339.07, 339.08
See application file for complete search history.

(56) References Cited

FOREIGN PATENT DOCUMENTS

| | | |
|---|---|---|
| DE | 39 37 554 A1 | 8/1990 |
| DE | 43 33 560 A1 | 4/1995 |
| GB | 1 604 691 A | 12/1981 |

(Continued)

OTHER PUBLICATIONS

"Ultrasonic Standing Wave Accelerates On-Line Measurement and Prevents Coating of a FTIR ATR Flow Cell", Proc. 2004 IEEE Sensors vol. 2, Vienna, Austria, p. 757-759, to Radel et al.*

(Continued)

*Primary Examiner* — Mark R Gaworecki
*Assistant Examiner* — Kenneth J Malkowski
(74) *Attorney, Agent, or Firm* — Joyce von Natzmer; Agris & von Natzmer LLP (57) ABSTRACT

The invention relates to a device (1) for FTIR absorption spectroscopy, having an ATR sensor (5) and at least one ultrasonic transmitter (10) for generating an ultrasonic field in the manner of a standing wave. The ATR sensor (5) and the ultrasonic transmitter (10) are connected to a mounting (4) which is provided for attachment in a wall (2) or cover of a reactor (3) and which is set up to hold the ATR sensor (5) and the ultrasonic transmitter (10) so that they freely project into the interior of the reactor (3) in the mounted state.

15 Claims, 7 Drawing Sheets

(56) References Cited

FOREIGN PATENT DOCUMENTS

| GB | 2 228 083 A | | 8/1990 |
| GB | 2228083 A | * | 8/1990 |
| JP | 4332852 A | | 11/1992 |
| WO | 2005/124300 A1 | | 12/2005 |

OTHER PUBLICATIONS

Radel S et al: "Ultrasonic particle manipulation exploited in on-line infrared spectroscopy of (cell) suspensions" in: Elektrotechnik Und Informationstechnik, vol. 125, No. 3, Mar. 1, 2008, pp. 76-81.

* cited by examiner

DEVICE FOR FTIR ABSORPTION SPECTROSCOPY

This is the U.S. national stage of International application PCT/AT2010/000006, filed Jan. 8, 2010 designating the United States and claims priority to Austrian applications AT 26/2009, filed Jan. 8, 2009 and AT 30/2009, filed Jan. 9, 2009.

FIELD OF THE INVENTION

The description relates to a device for FTIR absorption spectroscopy, having an ATR sensor and at least one ultrasonic transmitter for generating an ultrasonic field in the manner of a standing wave.

BACKGROUND OF THE INVENTION

Absorption spectroscopy, in particular with the aid of infrared [radiation], is often used for identifying certain substances, for example in the course of process monitoring. For this purpose, according to the prior art flow cells are used, through which the substances to be detected are led with the aid of carrier liquids. The use of an FTIR ATR flow cell (FTIR: Fourier transformation infrared; ATR: attenuated total reflection) for such process monitoring has been proposed in WO 02/082061 A and WO 2005/124300 A; a sensor element in the form of an ATR crystal, such as a diamond, is used in which total reflection of introduced infrared radiation occurs during the spectroscopy, wherein the total reflection at the boundary surfaces of the ATR crystal is damped (attenuated) as a function of the deposition (sedimentation) of the substances (particles) to be detected. One problem is that the sensor used in the flow cell may become contaminated by the substances, in particular when biotechnological processes or fermentation processes are involved, which must be monitored; the substances produced in a fermentation medium and their contents, as well as microorganisms and their physiological status, may be monitored. For cleaning the ATR crystal, a chemical cleaning method has typically been used in the past in which the flow cell is rinsed with appropriate cleaning substances. However, removing such polymeric or organic deposits (often also referred to as biofilm) from the optical sensor, i.e., in particular from the diamond window of an ATR element, using wash solutions requires relatively long cleaning times. This problem of film formation on the sensor surface has also been addressed in U.S. Pat. No. 5,604,132 A, in which physical cleaning in the form of stripping is indicated; however, this method is likewise complicated, and problematic with respect to the sensitive crystal surfaces.

According to WO 2005/124300 A cited above, it is further provided to generate ultrasonic standing waves for particle manipulation in order to improve the measurement or for cleaning the sensor surfaces. Such ultrasonic fields in the form of "quasi-standing waves" are easily controlled, and when piezo converters (piezo transducers) are used, which is the preferred case, the ultrasonic field is easily controllable with regard to frequency and amplitude by appropriately adjusting the electrical signal which actuates the particular piezo converter. To obtain the desired spatial standing wave, the emitted ultrasonic wave may be reflected on the opposite side of the flow cell, at the ATR sensor, for example, the returning wave being superimposed by the emitted wave, thus forming the standing wave. In this standing wave the envelope curve of the amplitude is stationary in the direction of sound propagation, i.e., is constant over time.

For such an ultrasonic standing wave, axial (primary) acoustic radiation forces act on deposited particles which are present in the flow cell, in particular at the sensor surface; the effect on the particles, for example cells such as yeast cells, is such that these particles are pushed in the direction of the pressure nodes of the standing wave field. Accordingly, the particles suspended in the carrier liquid are concentrated in planes parallel to the piezo transducer surface, namely, in the pressure node plane(s). Since the ultrasonic field is generally stronger, for example, in the middle than at the edge due to the fact that the ultrasound generation in the piezo transducer is not totally homogeneous, transversal primary acoustic radiation forces also act on the particles, which, depending on the concentration of the particles in the pressure node planes, results in forces being exerted on the particles in the direction of specified locations (for example, the axis of the flow cell) inside these planes, resulting in intensified agglomeration of the particles at these locations in the pressure node planes; as a result, a type of chain of particle agglomerates is obtained. This concentration of the particles, i.e., these agglomerates, remain(s) as long as the ultrasonic field is switched on. When the ultrasonic field is deactivated, the particles are transported from the flow cell due to the liquid flow.

In carrying out the spectroscopy according to this known technique, the particle agglomerates also have a shorter sedimentation time than individual cells, so that quicker measurements, in shorter successive intervals, are possible as the result of the shortened sedimentation time; on the other hand, the interfering sedimentation of particles on the sensor surface (biofilm formation) is counteracted. Tests have shown that when the particles are held in a floating manner above the sensor element for a period of 30 s, for example, by activating the ultrasonic field before falling onto the sensor surface, and agglomerated, the resulting particle agglomerate sediments significantly faster than individual particles.

Although this known technique according to WO 2005/124300 A has proven to be suitable, it is disadvantageous that a dedicated flow cell is used, which makes it necessary for a bioreactor, for example, which is used for carrying out a process to be monitored, to deliver the substances to be measured in dedicated lines of the flow cell, from which the substances are once again returned to the bioreactor. This means an additional outlay of equipment, and a further disadvantage results in the described sedimentation technique, according to which the sedimentation of particles on the surface of the ATR sensor must be awaited before a specific measurement is carried out. In addition, a change in the chemical parameters could result due to the transport of the substances to the measuring location outside the bioreactor.

On the other hand, a device has been proposed in DE 43 33 560 A1 for continuous spectroscopic analysis according to the principle of attenuated total reflection, in which an ultrasound source situated in the vicinity of the measuring surface is used to clean product residues from the measuring surface of an ATR element. In particular, the ultrasound source generates ultrasonic waves which are directed toward the measuring surface. In one embodiment having a built-in probe which is fixed to a reactor wall via a flange connection, a reflector for increasing the ultrasonic intensity is associated with the ultrasound source; however, a standing wave is not generated.

Lastly, U.S. Pat. No. 5,604,132 A describes monitoring of a chemical process with the aid of an infrared detector provided in a dedicated circuit, whereby samples of the reaction mixture are periodically injected into a liquid carrier stream and supplied to the IR detector. However, this has nothing to do with FTIR absorption spectroscopy.

SUMMARY OF THE INVENTION

The object of the invention is to further improve the technique by which standing waves are generated, and in particular to allow direct measurements for monitoring processes with minimum complexity, a further aim being to speed up the measurement process so that sedimentation of particles onto the sensor surface is no longer necessary.

This object is achieved according to the invention by a device for FTIR absorption spectroscopy as defined in Claim 1. Advantageous embodiments and refinements are stated in the dependent claims.

The invention in particular provides that the ATR sensor and the ultrasonic transmitter are connected to a mounting which is provided for attachment in an opening in a wall or cover of a reactor, the mounting holding the ATR sensor and the ultrasonic transmitter, via tubes, so that they freely project into the interior of the reactor in the mounted state.

In the present FTIR absorption spectroscopy device, the ATR sensor and the ultrasonic transmitter thus freely project into the interior of the reactor in the mounted state, and are held against the wall or cover of the reactor with the aid of the mounting. The desired measurement or process monitoring may thus be carried out directly inside the reactor, so that the desired process parameters may be directly obtained with minimum outlay of equipment. It would also be possible to mount the ultrasonic transmitter above the ATR sensor, i.e., at its sensor surface, and to allow the agglomerated particles to be detected to sediment on the sensor surface in a manner known per se (see WO 2005/124300 A1). However, in such a reactor a stirring device, for example a rotor which has stirring blades and is situated at the bottom and externally driven by a shaft, optionally also a magnetic stirrer, is usually used, so that the contained liquid is subjected to flow and mixing. As a result, however, unlike the case for an external flow cell mounted in a shunt (bypass) line, the measurement cannot be carried out simply on the basis of such sedimentation. In this case it is advantageous for the ultrasonic transmitter to be connected to a frequency adjusting unit in order to change the position of the standing wave in the measuring range between the ultrasonic transmitter and the ATR sensor by regulating the frequency, and in particular to press a pressure node plane, in which the particles have collected in agglomerates, against the surface of the ATR sensor. This has the further advantage that the ultrasonic transmitter and the ATR sensor may then be mounted in horizontal alignment with one another, which, among other things, simplifies installation of the mounting to the ATR sensor and to the ultrasonic transmitter in the opening of the reactor wall, optionally also in the reactor cover.

In the active measuring phase, when the pressure node plane is to be pushed against the ATR sensor surface, the ultrasonic frequency may be just under 2 MHz, for example 1.8 or 1.9 MHz, depending on the substance to be measured; in the measuring pauses the frequency may be decreased by an order of magnitude to approximately one-tenth, for example, to approximately 170 kHz, or even completely switched off, resulting in a change in the substance in the measuring range as a result of the flowing liquid, with the aid of the stirring device, in particular the magnetic stirrer.

To generate the standing wave, opposite the ultrasonic transmitter an ultrasonic reflector, optionally also an identical ultrasonic transmitter, may be provided, thus providing means for generating a standing wave by superimposition of the ultrasonic waves. As known from WO 2005/124300, the ultrasonic reflector may be formed by the ATR sensor itself, or by a sound reflector surface situated behind same. An extremely simple overall design of the actual measuring system of the present absorption spectroscopy device is thus obtained.

A standard Ingold connector may be easily used for the mounting.

The support for the ultrasonic transmitter may be formed by a tube, the necessary electrical lines running inside the tube. The ultrasonic transmitter itself may be formed in a customary manner by a piezoelectric element (piezo converter, piezo transducer) mounted on a Macor (a machinable glass ceramic) or glass plate support, the piezoelectric element being provided with the appropriate electrodes in order to produce the mechanical vibrations, necessary for generating the ultrasonic waves, when an electrical voltage is applied. In this regard, reference may also be made to WO 2005/124300 A1.

A conventional design may also be selected for the ATR sensor, optical fibers (fiber optics) preferably being used for supplying infrared radiation from an interferometer to an ATR element of the sensor and for returning the infrared radiation to a detector after being influenced by the measured substances in the ATR element. However, direct injection into the ATR element is also possible.

Various materials may be used for the ATR elements, such as diamond as well as ZnSe, ZnS, Ge, Si, sapphire, KRS-5, silver halides (AgX), etc., all of these materials sharing the common feature that they are transparent in the spectral range of interest, and that they have a sufficiently high index of refraction. In the medium infrared range, diamond and ZnSe, for example, have an index of refraction of approximately 2.4, and for germanium the index of refraction is 4.0.

In order to adapt to the particular conditions in a bioreactor, for example, which affect the substances to be measured, it may also be advantageous when the ATR sensor and the ultrasonic transmitter are held by the mounting so that they are adjustable relative to one another. The ATR sensor is preferably adjustable relative to the mounting and relative to the ultrasonic transmitter, for example with the aid of a micrometer screw. However, it is noted that such adjustability may also be dispensed with for fixed applications of the present device.

For various applications it may also be advantageous to laterally mount the actual piezo converter, and to set an oscillator, situated opposite from the ATR sensor, into vibration via mode conversion in order to emit the ultrasonic waves in the direction of the ATR sensor. Accordingly, one advantageous embodiment is characterized in that the ultrasonic transmitter is provided with a vibrating plate which is connected to the ATR sensor and which is connected to a support, situated at an angle thereto, on which a piezo converter is mounted.

In the prior art, in addition to ATR elements for the ATR sensor which are infrared-sensitive on the end face there are also frustoconical ATR elements which are infrared-sensitive on the side (not on the end face). To be able to use such ATR elements within the scope of the present device, namely, in the sense of bringing the substances to be measured toward the sensitive conical lateral surface, it has proven to be advantageous when the ATR sensor has a cover cap with an opening in which a tapering ATR element is situated. It is particularly advantageous when the opening has an annular wall which is oppositely inclined with respect to the taper of the ATR element. A favorable access region is thus provided for the substances to be measured. It has proven to be particularly advantageous for the wall of the opening and the lateral surface of the ATR element which is formed by the taper to define an angle of 90°.

In addition, to retard soiling of the sensor surface it is often advantageous for the ATR sensor to have an ATR element which is provided with a protective layer.

BRIEF DESCRIPTION OF THE DRAWINGS

The invention is explained in greater detail below with respect to one particularly preferred exemplary embodiment, illustrated in the drawings, which however is not limited to same. The drawings show the following.

DETAILED DESCRIPTION OF PREFERRED EMBODIMENTS

Figure 1:
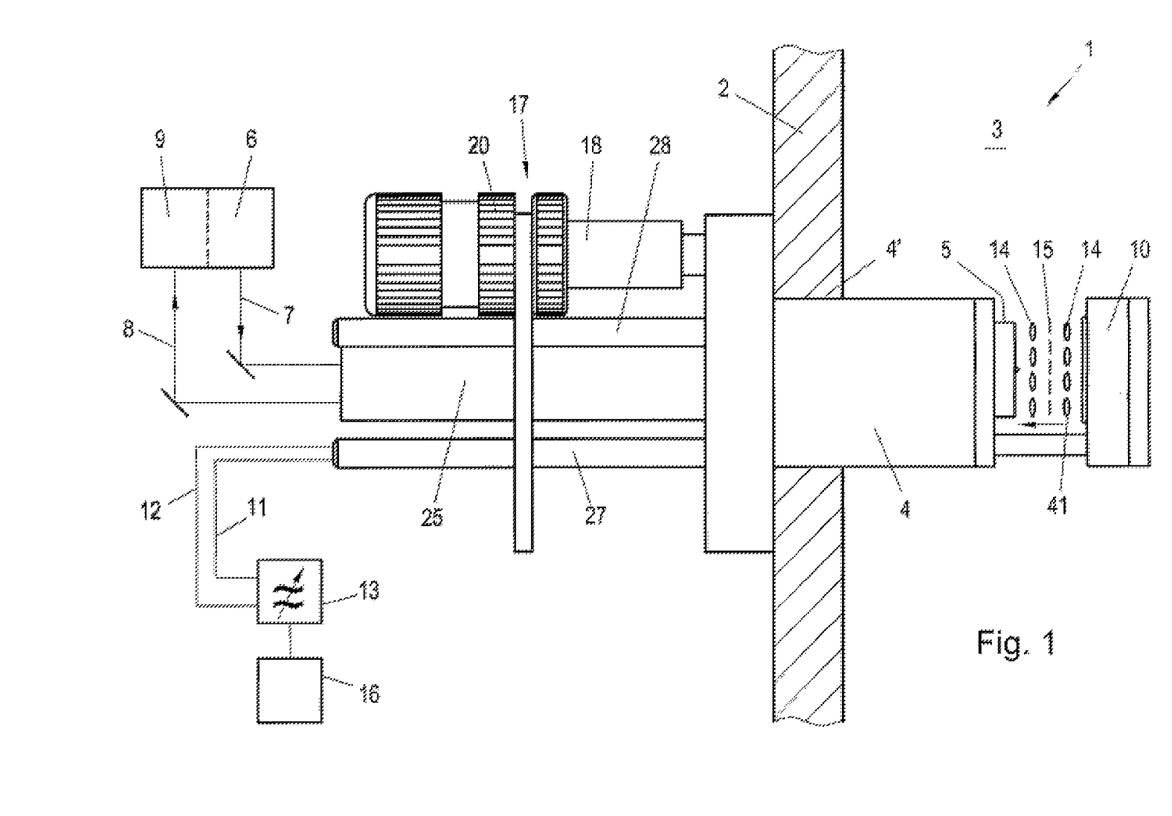
FIG. 1 schematically shows a cross section of part of a wall of a bioreactor together with a device according to the invention, having a mounting in an opening in the reactor wall, and measuring and probe elements supported by this mounting.
Figure 2:
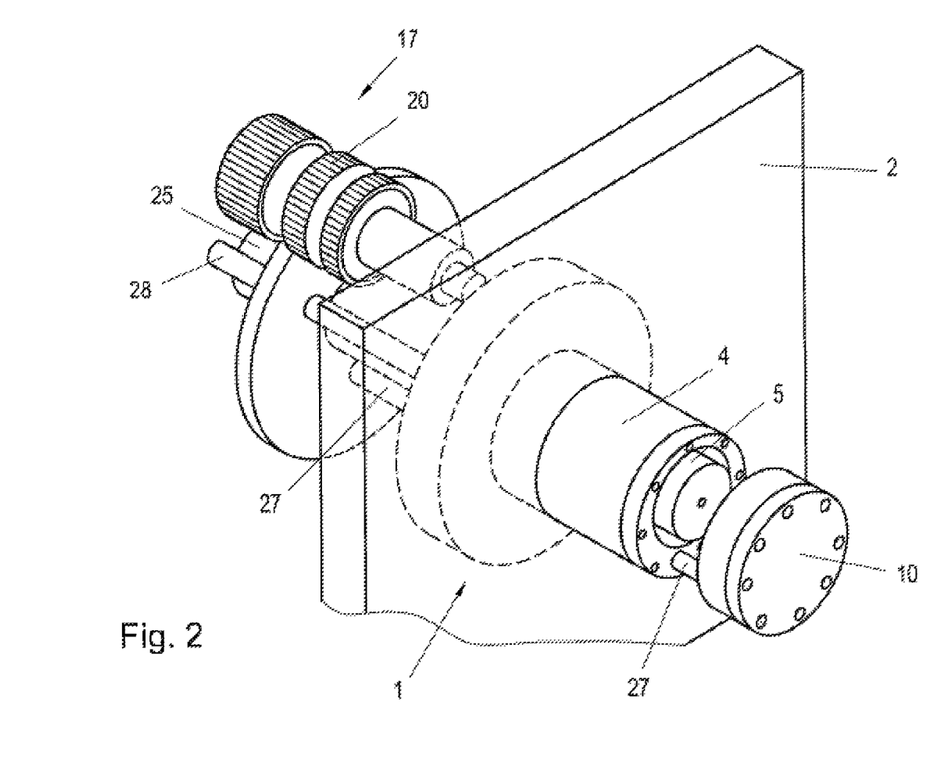
FIG. 2 shows a perspective view of the device according to FIG. 1.
Figure 3:
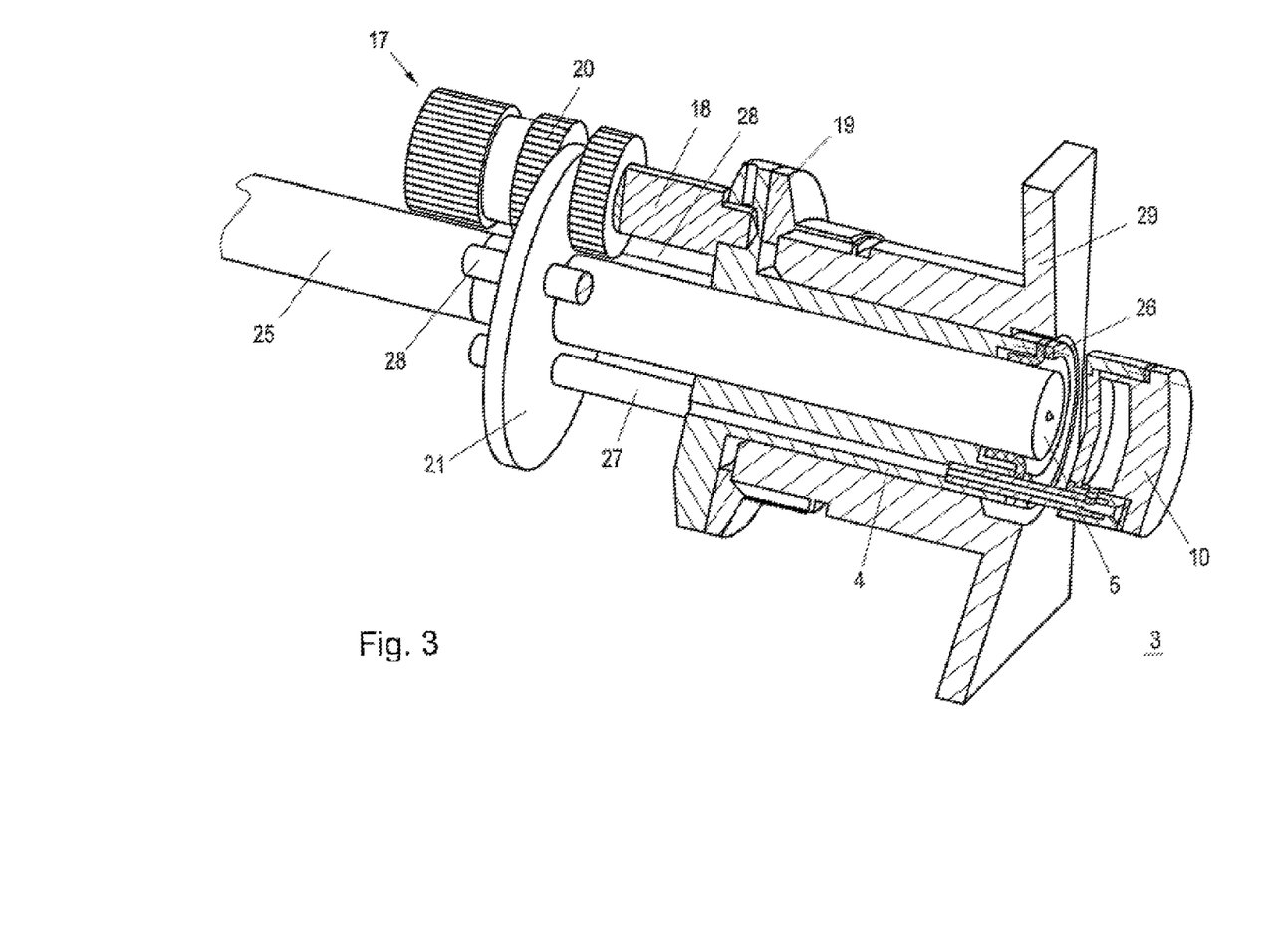
FIG. 3 shows a cutaway perspective illustration of this device according to FIGS. 1 and 2, for illustrating an adjustment option for the ATR sensor.

FIGS. 1 through 3 schematically illustrate an FTIR absorption spectroscopy device 1 having a basic design which corresponds to conventional devices used for IR spectroscopy, in particular FTIR ATR spectroscopy. This device 1 is mounted in a freely projecting manner to a wall 2 of a reactor 3 for carrying out the desired measurements, in particular a mounting 4 in the form of an Ingold connector being tightly fitted in an opening 4' in the reactor wall 2. The device 1 may be used to directly detect the substances to be investigated, in particular microorganisms such as yeast cells, in the monitoring of biotechnological processes in the reactor 3 in the course of the absorption spectroscopy.

A vertically situated ATR sensor 5 is located on the inner side of the mounting 4. Infrared radiation from an interferometer 6, for example, is supplied via an optical fiber 7 and via a zinc selenide element, for example, to a diamond which is provided as an ATR element (not illustrated in greater detail in FIGS. 1 through 3) of the ATR sensor 5, and is returned by the diamond to a detector 9 via an optical fiber 8. The ATR sensor 5 thus contains the ATR element (crystal element) as the actual sensor element for FTIR ATR spectroscopy; further explanation is unnecessary since this is a conventional technology. In this regard, reference is made in particular to WO 2005/124300 A and WO 02/082061 A, the disclosures of which are incorporated herein by reference. It is noted that various materials are used as ATR elements in ATR spectroscopy, such as the referenced diamond, as well as ZnSe, ZnS, Ge, Si, sapphire, KRS-5, silver halides (AgX), and similar materials which are transparent in the spectral range of interest and which have a suitable index of refraction.

Situated at a distance in front of the ATR sensor 5 (also referred to as "ATR probe" below) is an ultrasonic transmitter 10 (ultrasonic transducer or converter) which contains a ceramic piezoelectric element (not shown), for example, which is adhered to a plate-shaped Macor or glass support (not shown). The piezoelectric element has electrodes (not illustrated in greater detail) made of silver, for example, which are connected via electrical lines 11, 12 to a frequency generator 13, such as an FPS 4025 frequency power synthesizer, in order to produce a vibration in the range of 1.8 MHz to 1.9 MHz, for example. The electrical signal having this frequency is applied to the piezoelectric element, i.e., to the electrodes thereof, via the lines 11, 12, so that the piezoelectric element produces a corresponding ultrasonic vibration having a frequency of 1.8 MHz to 1.9 MHz, which is emitted via the glass support. According to the illustration in FIG. 1, this ultrasonic wave is emitted horizontally to the ATR sensor 5, whereby the ATR sensor 5 itself, for example, forms an ultrasonic reflector, and the ultrasonic wave is reflected back horizontally to the ultrasonic transmitter 10, resulting in a standing ultrasonic wave between components 10 and 5. In the device 1 an ultrasonic standing wave field is thus generated, which has pressure node planes 14 and pressure antinode planes 15, which for the flat standing wave field shown are separated by a distance of one-fourth wavelength (in a standing wave field, it is also known that pressure nodes correspond to the sound pressure antinodes, and conversely, pressure antinode locations correspond to the sound node locations). FIG. 1 schematically illustrates two pressure node planes 14 and one pressure antinode plane 15; of course, the number of pressure node planes 14 and pressure antinode planes 15 may vary, and the number of these node planes 14 or antinode planes 15 is a function of the speed of sound in the device 1, i.e., in the medium contained in the reactor 3, and in particular is a function of the spacing between the components 10, 5, and the frequency. For example, the spacing may be 3.18 mm. One-half the wavelength as the distance between two adjacent node planes 14, for example, may be in the range of 0.3 mm, for example. This would mean that approximately ten node planes 14 are formed between components 10, 5. Also conceivable, of course, are fewer node planes 14, for example merely one, two, or three, as well as more node planes 14, for example up to 100 node planes.

The device according to FIGS. 1 through 3 is also provided with the option of adjusting the ATR probe 5 and ultrasonic transmitter 10 relative to one another. In particular, the ATR sensor, i.e., the ATR probe 5, is axially adjustably supported in the mounting 4, as is apparent in particular from FIG. 3. To adjust the ATR probe 5 within the mounting 4, which is made of brass, for example, a micrometer screw drive 17 is provided, a micrometer screw 18 being supported on a flange 19 of the mounting 4 and fixedly coupled via its knurled adjusting nut 20 to a disk 21 which is fixedly connected to a cylindrical tube 25 of the ATR probe 5. The optical waveguides (optical fibers) of the ATR probe 5 are located in this tube 25, but for the sake of simplicity are not illustrated in greater detail in FIG. 3.

In the front region of the mounting 4, the probe, more precisely, the tube 25, is sealed from the interior of the reactor 3 by means of a diaphragm 26.

FIGS. 1 and 3 also illustrate the support tube 27 for the ultrasonic transmitter 10, as well as guide rods 28. In addition, FIG. 3 shows a connecting part 29 which is part of the wall 2 of the bioreactor 3; this connecting part 29 forms a standardized opening for the mounting 4 in the sense of an Ingold connector, and the entire probe structure may be inserted into the bioreactor through this opening, as is apparent from FIG. 3.

In the described design, the micrometer screw 17 adjusts the ATR probe 5 via the tube 25 thereof, while the probe mounting 4 remains stationary. A movable seal with respect to the interior of the bioreactor 3 is achieved by means of the diaphragm 26 in the front region of the fiber probe. When the micrometer screw 17 is adjusted in the longitudinal direction, the ATR probe 5 together with the tube 25 is correspondingly displaced in the brass casing formed by the mounting 4. The mounting 4 is flush with the opening edge in the wall of the bioreactor 3, i.e., the connecting part 29.

For fixed applications, such adjustability as described above may actually be unnecessary, although it is advantageous when various suspensions or carrier liquids may be provided, also when great temperature changes or great changes in the particle concentration may be present during operation.

Figure 4:
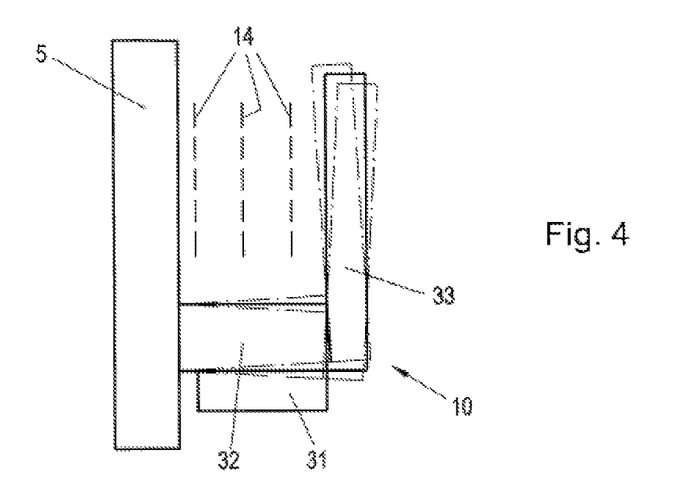
FIG. 4 schematically shows a modified configuration of the ultrasonic transducer or ultrasonic transmitter and the ATR sensor.

FIG. 4 schematically illustrates a modification of the probe head having the ATR sensor 5 and the ultrasonic transmitter 10. In this exemplary embodiment, the ultrasonic transmitter 10 is provided with a piezoelectric element 31 which is situated transversely with respect to the sensor surface and is mounted as a support 32 designed as an oscillator, the deflections of which are schematically indicated by various contour lines in FIG. 4. A vibrating plate 33 is mounted transversely with respect to this support 32, which is wall-shaped, for example; the main surface of the vibrating plate is situated opposite from the end face of the ATR sensor 5, and during operation is set into corresponding vibration by the piezoelectric element 31 via the support 32, as likewise schematically indicated by multiple contour lines in FIG. 4. An approximately flat sound wave is thus generated, which is emitted in the direction of the ATR probe 5. When the sound wave is reflected at the end face of the ATR probe 5, the superimposition of the two ultrasonic waves generates a standing wave having pressure node planes 14, as mentioned.

Figure 5:
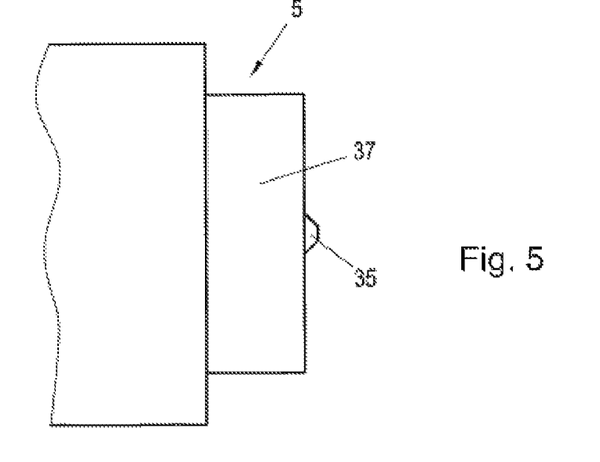
FIG. 5 shows a detailed perspective view of the ATR probe in an embodiment having a frustoconical ATR element situated in a cylindrical cap.
Figures 6, 7:
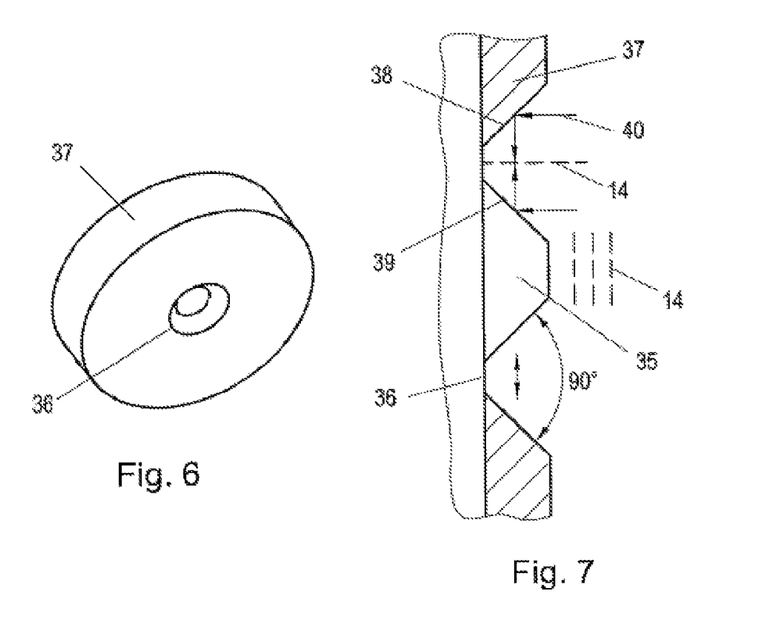
FIG. 6 shows the cylindrical cap used for this ATR sensor according to FIG. 5, in a perspective view.
FIG. 7 shows a schematic cross section of the region having the frustoconical ATR element which projects through the opening in the cap.

As stated above, the ATR sensor 5 may be designed as described in aforementioned WO 2005/124300 A, for example, namely, in particular having a planar infrared-sensitive ATR element on the end face. Another option is shown in FIGS. 5 through 7. In this design, a frustoconical ATR element 35 is provided which projects through a central opening 36 in a cap 37 which is cylindrical, for example. The opening 36 has an oppositely inclined annular wall 38, whereby the conical lateral surface 39 of the ATR element 35 and the annular wall 38 of the opening 36 in particular define an angle of 90°, as is apparent from FIG. 7. In the present case, the lateral surface 39 of the ATR element 35 is the infrared-sensitive sensor surface (and not the front end face; in this regard, the pressure node planes 14 would not provide a measuring result at this end face). However, as shown by the arrows in FIG. 7, the incident ultrasonic waves 40 are reflected at the bevels of faces 38, 39 which are inclined by 45° with respect to the vertical, whereby standing waves having pressure node planes 14 are likewise obviously able to form in the annular interspace between the faces 38, 39 (having a wedge-shaped cross section). The particles to be measured are then held in these pressure node planes 14, and may be detected due to their proximity to or contact with the ATR element 35.

Of course, such a system having a cap 37 is not necessary when an ATR element which is sensitive on its end face is used (see WO 2005/124300 A, for example). Particles, for example polymer beads, which are suspended in the liquid in the reactor 3 collect, as mentioned, in the pressure node planes 14 of the standing ultrasonic waves. Particle agglomerates 41 (see FIG. 1) form primarily in a central region relative to the ultrasonic transmitter 10 and the ATR sensor 5, i.e., in the vicinity of a center axis of these two coaxially aligned components 10, 5, since the particles are concentrated in the ultrasonic standing wave field in the pressure node planes 14, in particular due to the effect of axial primary acoustic radiation forces which act on the particles, and also due to transversal primary acoustic radiation forces which result due to the fact that the ultrasonic field is generally stronger at specified locations, for example in the middle, than in the edge regions. A type of chain of particle agglomerates thus forms in the particular pressure node plane 14.

It is mentioned at this point that the concentration of particles on an axis is a case by way of example which results from cylindrical symmetry and an appropriate electrode shape; of course, designs having multiple such "hot spots" are also possible when maxima of the transversal acoustic radiation force occur via the piezo converter surface.

Figure 8A:
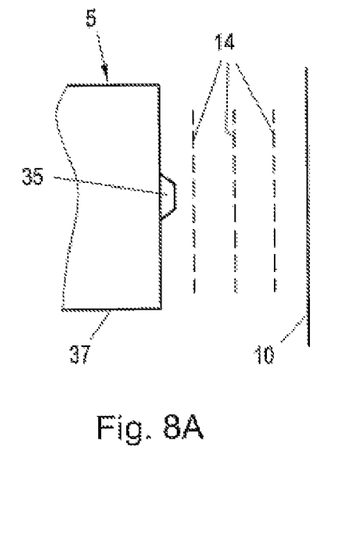
FIGS. 8A and 8B show views corresponding to FIG. 5, showing the agglomeration of particles in pressure node planes, whereby according to FIG. 8A the particles to be measured are still at a distance in front of the ATR element but do not contact same; however, in the illustration according to FIG. 8B, the particles to be measured are shown pressed against the ATR element after the change in the frequency of the ultrasonic field.
Figure 8B:
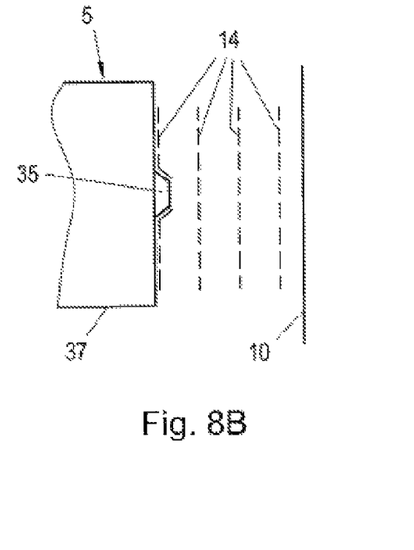

At a frequency $f_2$=1869 MHz (see FIG. 8B and FIG. 9), almost all particles of the first pressure node plane 14 were pressed against the ATR element 35 of the sensor 5.

In this manner the pressed particles are optimally subjected to spectroscopy, using the ATR (fiber) probe 5, in order to obtain sequences of sequentially recorded spectra, i.e., infrared absorption spectra concerning the suspended particles pressed against the sensor surface.

This spectroscopic analysis, in the case of a reactor 3 having a (conventional, not illustrated in greater detail) stirring device, in particular a magnetic stirrer, is preferably carried out as follows.

After the suspended particles deposit on the ATR element 35 and the ATR absorption spectroscopy is carried out, for example at a frequency of $f_2$=1.87 MHz, the frequency of the ultrasonic field is reduced to 170 kHz (see FIG. 9, region 42), which results in flows in the suspension which are suitable for rinsing away particles which were previously pressed against the ATR element; the absorption on the ATR element of the ATR sensor 5 thus drops practically to zero (except for the absorption which results from the liquid itself, which is not zero).

The frequency of the ultrasonic field is then increased back to the MHz range, resulting once again in sedimentation of the particles on the sensor surface at a frequency of $f_2$=1.87 MHz, and the absorption thus increases. The frequency is again reduced to 170 kHz, for example, in order to rinse away the sedimented particles.

Instead of the reduction to 170 kHz, the ultrasonic frequency may be switched off altogether.

The particles may thus be guided to the ATR sensor 5 in a controlled manner with the aid of the ultrasonic field, subjected to spectroscopy, and subsequently removed.

With regard to the rinsing away of the particles and the subsequent guiding of suspended particles into the measuring range, in tests it has also proven advantageous to temporarily increase the rotational speed of the magnetic stirrer, for example for approximately five seconds, during the pause times; it has been shown that increased sedimentation of particles on the sensor surface, and therefore stronger absorption, results when the ultrasonic field is applied for the absorption spectroscopy. One reason for this may be that small air bubbles were present in the liquid which initially prevented sedimentation of the particles, and were moved away by the ATR element 35 due to the increased stirring speed; the increased rotational speed during the tests could also intensify the guiding of particles into the measuring range of the device 1 from other regions in the reactor 3. For example, in the tests the normal rotational speed of the magnetic stirrer was approximately 280 rpm, and this rotational speed was temporarily increased to a value in the range of 800 rpm.

Figure 9:
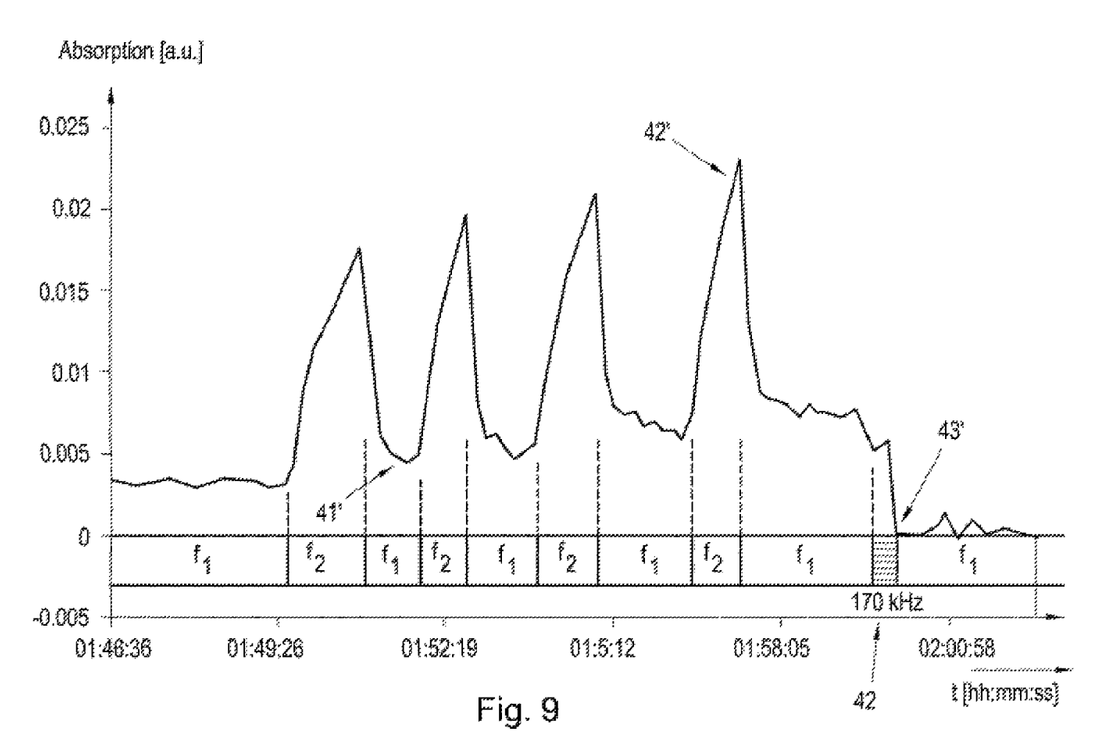
FIG. 9 shows a diagram as an example of the change over time of the peak height of a yeast absorption band at 1050 $cm^{-1}$, with an illustration of the change in the frequencies during this period.
Figure 10:
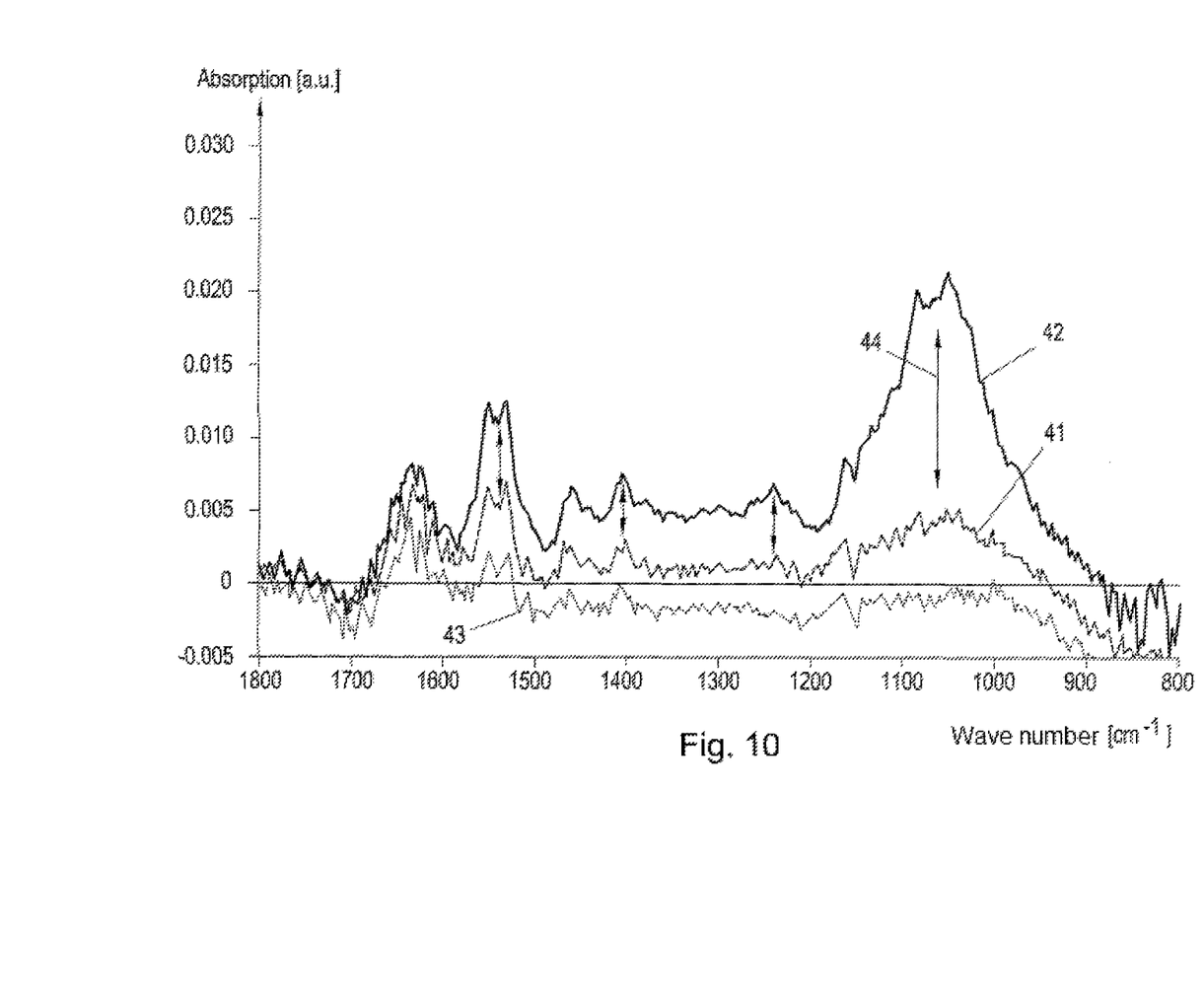
FIG. 10 shows a diagram of IR absorption measurements of yeast in water under the action of a standing ultrasonic wave, the state being illustrated in a curve in which the particles are still at a distance from the ATR element (see FIG. 8A), the state being shown for another curve according to FIG. 8B, with particles pressed against the ATR element, and a measurement during rinsing of the sensor surface being shown in a third curve.

The diagrams according to FIGS. 9 and 10 refer to examples of test measurements, namely, IR absorption measurements of yeast in $H_2O$, under the effect of standing ultrasonic waves. FIG. 9 illustrates the variation over time of the peak height of the yeast absorption band at a wave number of 1050 $cm^{-1}$, in which measurements were carried out at certain times as indicated on the abscissa. Specifically, a measurement was made at 01:51:33, at a time at which the frequency of the ultrasonic waves was $f_1$, and also at time 01:57:13 at a frequency $f_2$, as explained above, with the particle agglomerates pressed against the ATR element, and lastly, at a time 02:00:13 during rinsing at 170 kHz in region 42 according to FIG. 9. The absorption is illustrated in arbitrary units in FIGS. 9 and 10. The times of taking the measurement are indicated by 41', 42', and 43' in FIG. 9, and the corresponding measurement curves are curves 41, 42, and 43 in FIG. 10.

The frequencies $f_1$ and $f_2$ generally indicate two different frequencies of the ultrasonic field, in which the keeping of particles away from the ATR element (frequency $f_1$) and the pressing of suspended, agglomerated particles (frequency $f_2$) occur as stated above. Of course, the frequencies may vary from the values stated above as examples, depending on the measured substance. The frequencies $f_1$ and $f_2$ are also a function of the resonator length, i.e., the distance between the end face of the ultrasonic transmitter 10 and the end face of the ATR sensor 5. At frequency $f_1$ the suspended particles, as mentioned, are still at a distance from the sensor surface, so that a low absorption in the IR spectrum is recorded in the measurement. When frequency $f_2$ is applied, the spatial distribution of force in the ultrasonic field changes, and the suspended particles are moved toward the ATR sensor, i.e., pressed into its detection range (see FIGS. 5 through 7), resulting in high absorption in the IR spectrum. This is also apparent from a comparison of curves 41 and 42 in FIG. 10, where the differences in the obtained absorption values are indicated by arrows, for example arrow 44. As mentioned, frequencies $f_1$ and $f_2$ may differ from the values stated above as examples, depending on the circumstances; in particular, these frequencies were $f_2=1.878$ MHz and $f_1=1.863$ MHz in the test measurements according to FIGS. 9 and 10. As a rule, the usable frequencies are in the range between 1.7 MHz and 2 MHz; this range may change, for example, when other piezoceramic materials are used for the ultrasonic transmitter (different speed of sound), or also for a different design (for example, when the thickness of the piezo converter or the support is different). In practice, the particular frequency range is based on the desired use, i.e., of the suspended liquid, the particles, the speed of sound in these two components, the size of the particles, etc., and optionally also the damping.

For the test measurements it would be expected, in principle, that a zero line would be obtained when frequency $f_1$ was applied (see curve 41 in FIG. 10); the fact that this does not occur is attributed to the soiling of the ATR element due to the fairly long measuring period. The third curve 43 shows a measuring result for when the ATR element of the ATR sensor 5 was cleaned at a much lower ultrasonic frequency of 170 kHz, resulting in significantly lower absorption values.

With regard to the soiling of the ATR element, it may also be advantageous to use an ATR element having a thin protective layer (for example, having a thickness of a few nm to approximately 1 μm). Such protective layers may retard the formation of soiling layers, and therefore may be advantageously used in some circumstances. One example of such is the formation of so-called "self-assembling monolayers" (SAM) on Si or Ge.

When the particle concentration is low, it is possible that the particles from the volume between two pressure node planes, after appropriate agglomeration, are not adequate to deliver a reliable optical measuring signal. In that case it is advantageous to use drifting resonance field (DRF) separation to guide additional particles to the sensor surface. In this technique, a jump is made from one resonance frequency to another while ensuring that the locations at which particles collect always lie "in one direction." After a cycle of several resonance frequencies, the agglomerates migrate slightly more than one-half wavelength, and the first resonance frequency may be started once again. This causes additional particles to be transported to a given location (the sensor surface).

This approaching motion of particles in an ultrasonic field is known from the article by B. Handl et al., "Particle trajectories in a drifting resonance field separation device," JASA 103 (1998): 2947-2975. This technique is advantageous for the present device, since the quality of the measurement depends on the densest coverage possible of the ATR sensor 5 with particles.

The invention claimed is:

1. Device for FTIR absorption spectroscopy, comprising
an ATR sensor and at least one ultrasonic transmitter for generating an ultrasonic field in form of a standing wave,
wherein the ATR sensor and the ultrasonic transmitter are connected to a mounting for attachment in an opening in a wall or cover of a reactor,
wherein the mounting holds the ATR sensor and the ultrasonic transmitter,
each via tubes which extend through the mounting to the ATR sensor and the ultrasonic transmitter, respectively, parallel to one another and which freely project into the interior of the reactor in the mounted state.

2. The device of claim 1, wherein the ultrasonic transmitter is connected to a frequency adjusting unit in order to move the position of a pressure node plane of the standing wave against the surface of the ATR sensor by adjusting the frequency.

3. The device of claim 2, wherein the frequency adjusting unit provides for the following three ultrasonic frequencies: approximately 1.8-1.9 MHz, approximately 170 kHz, and "off" (no amplitude), wherein the frequency adjusting unit is configured to allow a switch between these three ultrasonic frequencies.

4. The device of claim 2, wherein the ultrasonic transmitter is in horizontal alignment opposite the ATR sensor during operation.

5. The device of claim 1, wherein the ATR sensor forms an ultrasonic reflector.

6. The device of claim 1, wherein the mounting has an Ingold connector.

7. The device of claim 1, wherein the ATR sensor and the ultrasonic transmitter are held by the tubes so that they are adjustable relative to one another.

8. The device of claim 1, wherein the ultrasonic transmitter is provided with a vibrating plate which is connected to the ATR sensor, and which is connected to a support, situated at an angle thereto, on which a piezo converter is mounted.

9. The device of claim 1, wherein the ATR sensor has a cover cap with an opening in which a tapering ATR element is situated.

10. The device of claim 9, wherein the opening has an annular wall which is oppositely inclined with respect to the taper of the ATR element.

11. The device of claim 9, wherein the ATR sensor has an ATR element which is provided with a protective layer.

12. The device of claim 1, wherein the ATR sensor contains a diamond as the ATR element.

13. The device of claim 1, wherein ATR sensor and the at least one ultrasonic transmitter are at a distance from each other that fit not more than 100 node planes.

14. Device for FTIR absorption spectroscopy, comprising
an ATR sensor and at least one ultrasonic transmitter for generating an ultrasonic field in form of a standing wave,
wherein the ATR sensor and the ultrasonic transmitter are connected to a mounting for attachment in an opening in a wall or cover of a reactor, the mounting holding the ATR sensor and the ultrasonic transmitter, via tubes so that they freely project into the interior of the reactor in the mounted state, wherein the ATR sensor has a cover cap with an opening in which a tapering ATR element is situated, wherein the opening has an annular wall which is oppositely inclined with respect to the taper of the ATR element and, wherein the wall of the opening and the lateral surface of the ATR element which is formed by the taper define an angle of 90°.

15. Device for FTIR absorption spectroscopy,
comprising
an ATR sensor and at least one ultrasonic transmitter for generating an ultrasonic field in form of a standing wave,
wherein the ATR sensor and the at least one ultrasonic transmitter are connected to a mounting for attachment in an opening in a wall or cover of a reactor, wherein the mounting holds the ATR sensor and the ultrasonic transmitter, each via tubes which extend through the mounting to the ATR sensor and the ultrasonic transmitter, respectively, parallel to one another and which freely project into the interior of the reactor in the mounted state, wherein the ultrasonic transmitter is connected to a frequency adjusting unit and wherein the ultrasonic transmitter is configured to move the position of a pressure node plane of the standing wave against the surface of the ATR sensor.

* * * * *